United States Patent [19]
Custer et al.

[11] Patent Number: 6,136,593
[45] Date of Patent: Oct. 24, 2000

[54] ASTROCYTE APPARATUS FOR BIOPROCESSING A CIRCULATING FLUID

[75] Inventors: Linda Custer, Marlborough; Claudy Mullon, Framingham, both of Mass.; Roger Butterworth, Pointe Claire, Canada

[73] Assignee: Circe Biomedical, Inc., Lexington, Mass.

[21] Appl. No.: 09/379,076

[22] Filed: Aug. 23, 1999

[51] Int. Cl.[7] .................................................. C12M 1/12
[52] U.S. Cl. ............................................................ 435/297.4
[58] Field of Search ............................. 435/289.1, 297.4

[56] References Cited

U.S. PATENT DOCUMENTS 5,643,794   7/1997   Liu et al. ............................. 435/289.1

OTHER PUBLICATIONS

Booher, J. et al., "Growth and Cultivation of Dissociated Neurons and Glial Cells from Embryonic Chick, Rat and Human Brain in Flask Cultures," Neurobiology, vol. 2, pp. 97–105, 1972.

Butterworth, Roger F., "Portal–Systemic Encephalopathy: A Disorder of Neuron–Astrocytic Metabolic Trafficking," Dev Neurosci, vol. 15, pp. 313–319, 1993.

Norenberg, Michael D. et al., "Fine Structural Localization of Glutamine Synthetase in Astrocytes of Rat Brain," Brain Research, vol. 161, pp. 303–310, 1979.

*Primary Examiner*—David A. Redding
*Attorney, Agent, or Firm*—Fish & Richardson P.C.

[57] ABSTRACT

The invention relates to a container having astrocytes for use in removing toxins from a biological fluid. The container includes a first port for receiving the biological fluid and a second port through which the biological fluid exits the container. The invention also relates to a method of treating a biological fluid by contacting it with astrocytes.

18 Claims, 4 Drawing Sheets

ASTROCYTE APPARATUS FOR BIOPROCESSING A CIRCULATING FLUID

BACKGROUND OF THE INVENTION

Liver failure leads to the accumulation of toxins such as ammonia in the blood of patients. Apparatuses for removing these blood toxins (also called liver assist systems) have been developed and are grouped into passive or bioactive devices. Passive devices generally remove the toxins by hemodialysis, hemoperfusion, or plasma exchange, while bioactive devices can include living cells which remove or convert the blood toxins. An example of a bioactive liver assist system containing hepatocytes is described in U.S. Pat. No. 5,643,794.

SUMMARY OF THE INVENTION

The invention is based on the discovery that astrocytes can remove toxins from a biological fluid. Accordingly, the invention features a system for removing toxins from a biological fluid by treating the fluid with astrocytes. The system includes a first container having a first port for receiving the biological fluid, a second port through which the biological fluid exits the first container, and astrocytes residing in the first container. The system provides a means to contact a volume of fluid, significantly larger than the volume held by the container, with astrocytes by continuously passing portions of the fluid through the container via the first and second ports. Thus, a continuous flow system including the above container can be small relative to the volume of the fluid to be treated.

The system described above includes one or more of the following features. For example, the system can further include a conduit for circulating the biological fluid, the conduit being connected to the first port and second port. The conduit allows additional elements of the system to be connected to the system. These elements include (1) a pump connected within the conduit and adapted to circulate the biological fluid through the conduit; (2) a heater connected within the conduit and adapted to maintain the biological fluid within a temperature range; (3) an oxygenator connected within the conduit and adapted to supply oxygen to the biological fluid; (4) an inlet configured to receive the biological fluid from an external system (e.g., a plasma separation machine), and an outlet configured to return a portion of the biological fluid to the external system; and (5) a bypass structure which, upon actuation, prevents flow of the biological fluid between the conduit and the external system. Thus, the system for removing the toxins can be connected to an external system that, for example, separates debris and solid material from a biological fluid before it enters the toxin-removing system. The bypass structure is useful for diverting the biological fluid from the system when there is a catastrophic failure in the container. Such a failure may allow astrocytes to be intermixed with and to contaminate the fluid in the absence of the bypass structure.

In one particular embodiment, the system includes a second container connected within the conduit and having a third port for receiving the biological fluid, a fourth port through which the biological fluid exits the second container, and non-astrocyte cells (e.g., hepatocytes) residing in the second container. Alternatively, the non-astrocyte cells can reside in the first container along with the astrocytes. The non-astrocyte cells can assist the astrocytes in clearing toxins from the biological fluid. The first or second container can be a hollow fiber bioreactor such as that described in U.S. Pat. No. 5,643,794, in which case the biological fluid passes through a lumenal space of the hollow fibers and the cells reside outside of the lumenal space. The hollow fibers can be made of a semi-permeable membrane having pores with a diameter of less than about 2 µm (e.g., about 0.1 µm to 1 µm). In general, suitable membranes allow transport of solutes, including proteins such as albumin, and other molecules to reach cells so that cells can clear complexed toxins (albumin-bound toxins).

The above arrangement of hollow fibers prevents the loss of cells from the container and contamination of the biological fluid with the cells. However, a barrier such as hollow fibers is not necessary to prevent such loss or contamination. For example, the cells can adhere to an interior surface of the container, thereby preventing the loss of cells and contamination of the fluid. The cells also can be encapsulated.

Another aspect of the invention features a container which includes a first compartment for receiving the biological fluid, a second compartment adjacent to the first compartment, and a first porous barrier which separates the first compartment from the second compartment. The first porous barrier is impermeable to astrocytes residing in the second compartment.

The container can include a third compartment adjacent to the first compartment or second compartment, a second porous barrier which separates the third compartment from the first compartment or second compartment, the second porous barrier being impermeable to non-astrocyte cells, and non-astrocyte cells (e.g., hepatocytes) residing in the third compartment. Alternatively, the non-astrocyte cells can reside in the second compartment, in which case the first porous barrier is impermeable to the non-astrocyte cells as well as astrocytes. Non-astrocyte cells (e.g., hepatocytes) can facilitate the removal of similar or different toxins from the biological fluid, or aid in the viability or function of astrocytes. A porous barrier suitable for use with this container includes a metal mesh with pores small enough to block passage of astrocytes or other cells through the barrier. Other examples of porous barriers include membranes made of polyethylene, polypropylene, polycarbonate, teflon, cellulosics (such as cellulose acetate), polysulfone, polyether sulfone, polyvinyl alcohol, or polyacrylonitrile.

The invention also includes a method of treating a biological fluid suitable for administering to an animal by contacting the biological fluid with astrocytes, separating the biological fluid from the astrocytes, and administering (e.g., intravenously) the biological fluid to an animal. Optional features of the method include contacting the biological fluid with non-astrocyte cells (e.g., hepatocytes) and separating the biological fluid from the non-astrocyte cells. This method can be used to treat, for example, blood directly flowing from a patient blood vessel into the system described above and back to the patient, thereby treating (e.g., removing toxins from) the whole blood or a component thereof (e.g., plasma).

The biological fluid treatable in the above-described system, container, and method is any fluid that is derived from or suitable for delivery into an animal, especially a human. Such fluids include whole blood, plasma, serum, lymph, cerebralspinal fluid, and artificial or synthetic blood products. Astrocytes which are used to practice the invention include mammalian astrocytes, such as bovine, porcine, murine, rat, primate, and human astrocytes.

One of the most serious side-effects of liver failure (especially in acute liver failure) is bran swelling, which can lead to a coma or even death within a few days.

Unfortunately, the compounds causing this swelling is largely unknown. A key feature of the invention is the use of astrocytes, a cell type not previously recognized for its utility in devices and methods for removing a toxin (e.g., ammonia) from a biological fluid such as plasma. Thus, astrocytes are particularly useful for removing toxins from plasma in patients experiencing liver failure, thereby alleviating brain swelling.

Other features and advantages of the invention will become apparent from the following drawings and detailed description, and also from the claims.

DETAILED DESCRIPTION OF THE INVENTION

The invention relates to systems and containers having astrocytes for removing toxins from a biological fluid. The invention also includes methods of treating a biological fluid by contacting the fluid with astrocytes. Such systems, containers, and methods can be used to treat or prevent hepatic encephalopathy, an often fatal condition associated with acute liver failure.

Without further elaboration, it is believed that one skilled in the art can, based on the above disclosure and the description below, utilize the present invention to its fullest extent. The following description is to be construed as merely illustrative of how one skilled in the art can practice the invention and are not limitative of the remainder of the disclosure in any way. Any publications or patent applications cited in this disclosure are hereby incorporated by reference.

Hollow Fiber Container Having Astrocytes

Figure 1:
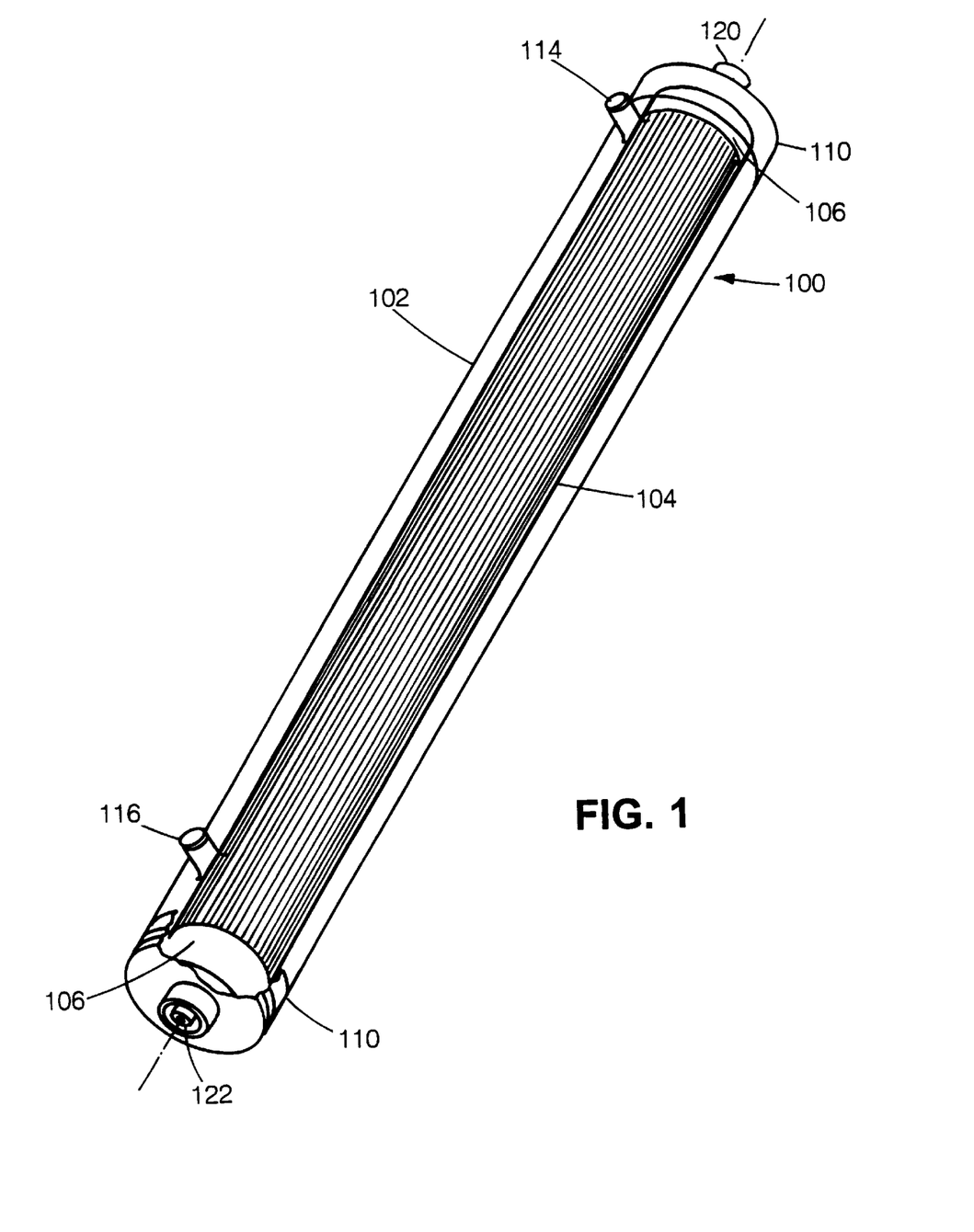
FIG. 1 is a diagrammatic view of a system of the invention for treating a biological fluid.

A hollow fiber container 100 suitable for removing toxins from a biological fluid is illustrated in FIG. 1. Hollow fiber container 100 includes a housing 102 having an interior within which a multiplicity of hollow fibers 104 made of semi-permeable membranes are disposed. At regions near each end of container 100, the spaces between hollow fibers 104 are filled with a liquid-impermeable potting material 106, e.g., epoxy or polycarbonate, which holds hollow fibers 104 in place and occupies an entire cross-section of container 100. Potting material 106 is disposed medially within container 100 with respect to the ends of the hollow fibers 104 so that the ends are between potting material 106 and the ends of container 100. Thus, an enclosure 108 (also see FIG. 2C) is formed by the inside surface of housing 102, the outside surfaces of hollow fibers 104, and potting material 106 near each end of container 100. This region of container 100 constituting the enclosure is referred to as the shell space, or, alternatively, extracapillary space.

Housing 102 can be made of any suitable biocompatible material, e.g., a plastic such as polystyrene or polyacrylonitrile. Housing 102 also includes plastic endcaps 110. Housing 102 has two laterally disposed ports 114 and 116 for introducing astrocytes 118 and a wash buffer (not shown) to enclosure 108 (FIG. 2C). When container 100 is ready for use, astrocytes 118 reside in enclosure 108 (FIG. 2C). Also shown are longitudinal inlet 120 and longitudinal outlet 122 at each end of housing 102. Longitudinal inlet 120 and outlet 122 lead to lumenal spaces 112 of hollow fibers 104. Thus, a biological fluid flowing into container 100 through inlet 120 and then out of container 100 through outlet 122 can be purified of small molecule toxins through the action of astrocytes 118 residing in enclosure 108.

To assemble container 100, hollow fibers 104 are cut to a length matching that of container 100 and placed inside housing 102 in a relatively dense or bundled packing. Potting material 106 is introduced into lateral ports 114, 116, and then directed to regions near the ends of housing 102, e.g., by centrifuging container 100.

Figure 2A:
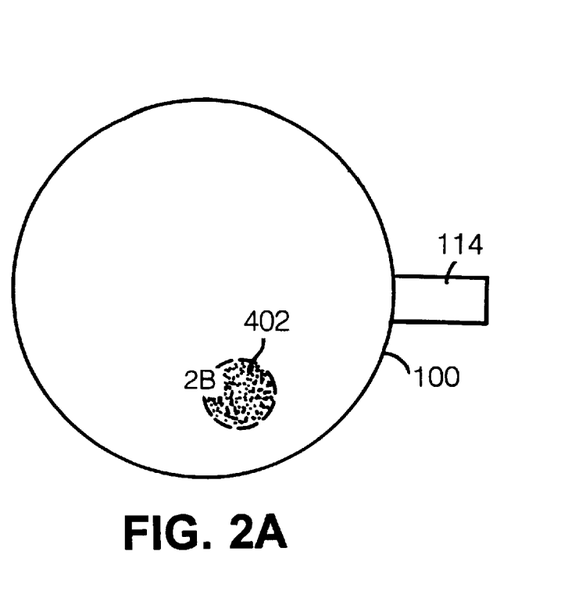
FIG. 2A is a cross-sectional top view of the system shown in FIG. 1.
Figure 2B:
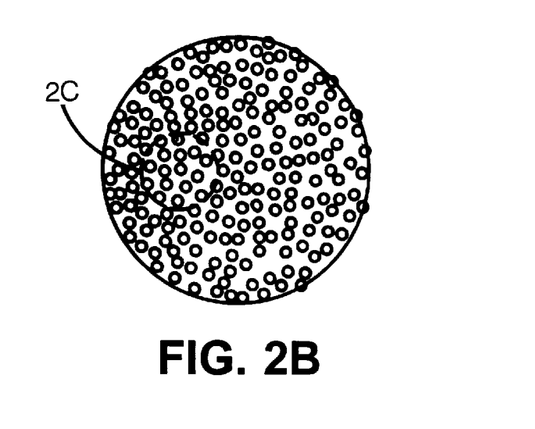
FIG. 2B is an enlargement of a portion of the system shown in FIG. 2A.
Figure 2C:
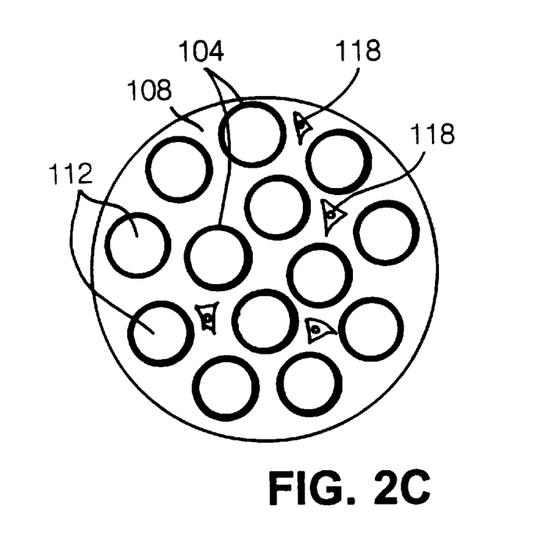
FIG. 2C is an enlargement of a portion of the system shown in FIG. 2B.

The way in which hollow fibers 104 in container 100 are arranged to produce enclosure 108 and lumenal spaces 112 is shown in FIGS. 2A–2C. Hollow fibers 104 of container 100 extend longitudinally within container 100, in a direction roughly parallel with the walls of housing 102. Hollow fibers 104 are approximately 270 $\mu$m inner diameter×310 $\mu$m outer diameter×450 mm length. A total of about 4300 hollow fibers can be positioned within container 100. Hollow fibers 104 are made of a membrane having a pore size (e.g., about 0.15 $\mu$m in diameter) completely excluding astrocytes from the biological fluid in lumenal spaces 112, while allowing passage of individual molecules into lumenal spaces 112 of hollow fibers 104 (FIG. 2C).

FIG. 2A is a cross-sectional slice through container 100, showing housing 102 and about 4300 hollow fibers 104. Also shown in FIG. 2A is port 114 through which astrocytes are introduced into enclosure 108. FIGS. 2B and 2C are serial expansions of regions containing and surrounding individual hollow fibers 104. FIG. 2C shows enclosure 108 and lumenal spaces 112 of hollow fibers 104. Further details of container 100 can be found in U.S. patent application Ser. No. 09/059,275.

Liver Assist System Containing Astrocytes

Figure 3:
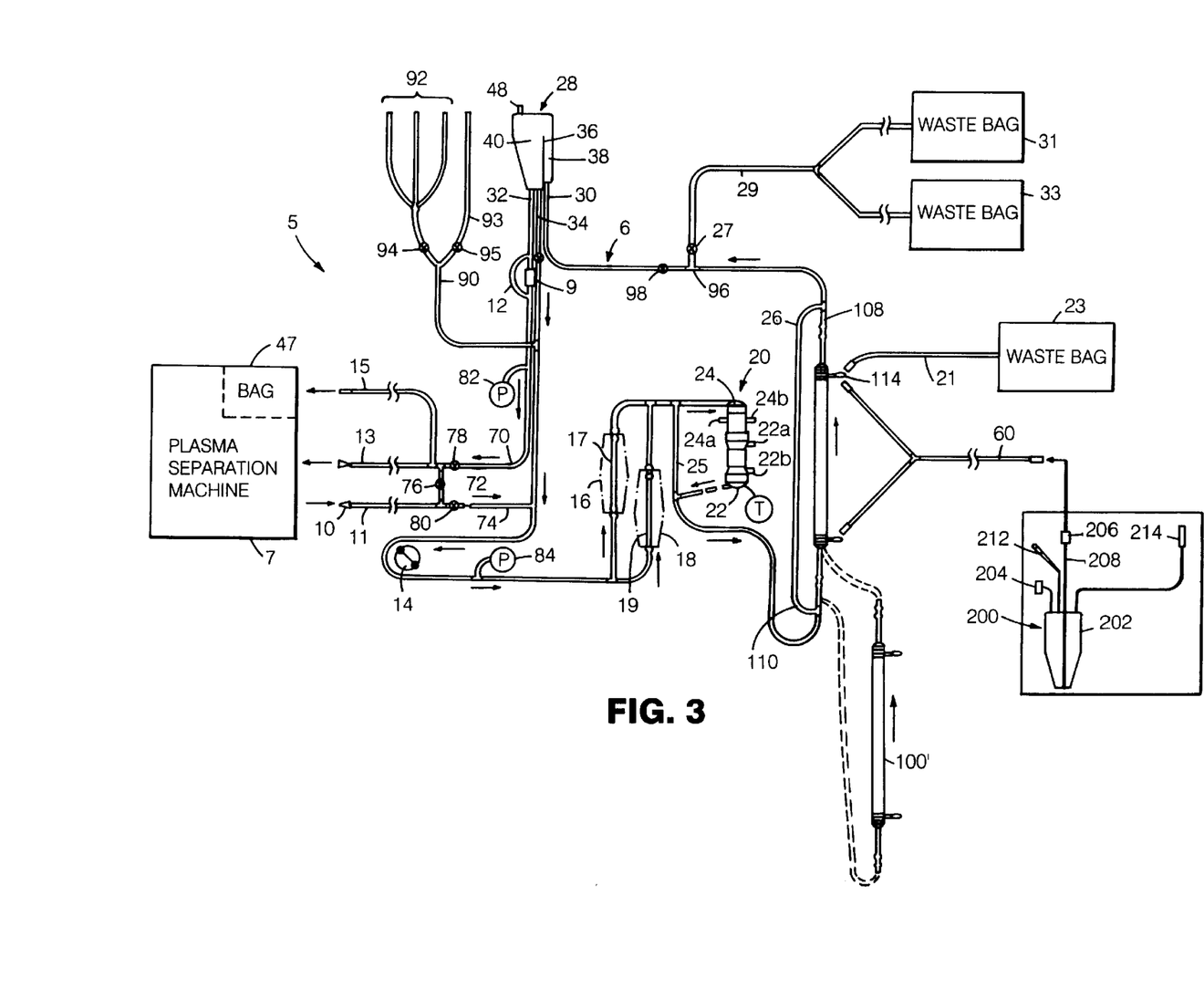
FIG. 3 is a diagrammatic view of a liver assist system utilizing the system for treating a biological fluid as shown in FIG. 1.

Container 100, as described above in conjunction with FIGS. 1 and 2A–2C, can be used as part of a liver assist system for removing toxic substances from plasma. Referring to FIG. 3, for example, container 100 is shown connected within a liver assist system 5 having a conduit 6 made of disposable plastic tubing (e.g., PVC) for circulating plasma. In certain applications, conduit 6 may include sections of tubing (11, 13, 70, 74) used to connect liver assist system 5 to an external system, such as a plasma separation machine 7. Connected within conduit 6, in a series arrangement, are a peristaltic pump 14, optional charcoal filters 16, 18, an oxygenator/heat exchange unit 20, container 100, and a reservoir bag 28, each of which will be discussed in greater detail below. In this embodiment, liver assist system 5, in use, supports approximately 650 ml of fluid with about 120 ml disposed within conduit 6. An optional second container 100' containing hepatocytes can also be connected in series to container 100 to facilitate removal of toxins from plasma. The toxins removed by hepatocytes can be the same or different from the toxins removed by the astrocytes.

Prior to introducing the plasma to liver assist system 5, saline (or other suitable fluid) is used to entirely fill conduit 6 as well as the components of the system. Reservoir bag 28 is also filled sufficiently to provide a buffer for incoming fluid and indicates when liver assist system is entirely filled and primed. This process is part of a cleansing process in which the system is rinsed and primed using a method described below.

In general, plasma is provided to the liver assist system 5 at an in-port 10 via tubing 11 and is pumped through the system using pump 14 in the direction indicated by arrows. Filters 16, 18 pre-filter the plasma of toxins while oxygenator/heat exchange unit 20 oxygenates and maintains the temperature of the plasma within a predetermined temperature range. The plasma is then received by container 100. The reservoir bag 28 receives the treated plasma before being recirculated back through the system.

Liver assist system 5 is generally used in conjunction with a cell inoculation device 200 (described below) which provides cells of various types to containers 100 or 100'. The inoculated cells can remove or modify toxic substances from the plasma. Alternatively, the cells can facilitate the detoxification activity or viability of other cells in the device.

In FIG. 3, liver assist system 5 is shown as part of an on-line system that is connected to an external plasma separation machine 7, which supplies plasma to the liver assist system 5 for treatment. The plasma from plasma separation machine 7 is provided to conduit 6 from tubing 11 and returned from liver assist system 5 via tubing 13.

Plasma separation machine 7 separates plasma to be treated from whole blood of a patient experiencing liver failure. In other on-line applications, the external system may be a patient and the whole blood of the patient is circulated and bioprocessed in liver assist system 5. It is also important to note that liver assist system 5 may be used in an off-line operation in which a source of plasma to be treated is provided, for example, in a bag and connected to an in-port 10 of the liver assist system 5. In this case, the untreated plasma is allowed to circulate through liver assist system 5 to be detoxified and then dispensed at an out-port of the system.

Disposed within conduit 6 is pump 14, which provides sufficient drive to force the plasma from tubing 11 to flow through conduit 6 in the direction indicated by the arrows. The plasma flows at a user selectable flow rate between 50 and 1000 ml/min (e.g., 400 ml/min). The system includes a pair of charcoal filters 16, 18 for pre-filtering the plasma before it is provided to container 100. Only one of filters 16, 18 is in use at any given time, the other being available to allow continued use of system 5 when one of the filters needs to be replaced. Clamps (not shown) are used to allow and/or restrict flow through one of filters 16, 18. Either one of charcoal filters 16, 18 may be replaced with a length of tube 17 or 19 to provide a bypass path around charcoal filter 16 or 18 when system 5 is in use.

Plasma flowing through filters 16, 18 passes to oxygenator/heat exchange unit 20 having an oxygenator 22 which supplies oxygen to the plasma and a heater 24. Oxygenator 22 receives, at inlet 22a, pressurized sterile gas (e.g., 30% $O_2$, 5% $CO_2$, 65% $N_2$) from an external gas source (not shown). The plasma passes through semipermeable hollow fibers disposed within oxygenator 22 to collect oxygen needed by astrocytes 118 (and other cells, if present) within container 100. An optional oxygen measurement system may be used to measure the difference between the oxygen content of the plasma entering and exiting container 100 to provide an indication of the effectiveness of oxygenator 22. The pressurized gas provided to the oxygenator passes through hydrophobic membranes disposed respectively at inlet 22a and outlet 22b.

Plasma flowing through heater 24 is maintained at a predetermined temperature (e.g., 37° C.) by heat conduction as it flows past a heat exchanger within the oxygenator 22. Heated water from an external water heater/recirculator (not shown) is received at inlet 24a of the heater and returned via outlet 24b for reheating. A bypass line 25 with a clamp (not shown) is provided to bypass oxygenator/heat exchange unit 20 and through the system to allow the cleaning or replacement of the oxygenator/heat exchange unit 20.

Plasma from oxygenator/heat exchange unit 20 is received by container 100. A bypass line 26 having a manual clamp is provided to bypass container 100, for example, when container 100 requires replacement, maintenance, or cleansing (described below). During operation of liver assist system 5, tubing 29 attached to waste bags 31, 33 (described below), is closed off from flow of plasma with pinch valve 27.

The treated plasma is then conveyed to plasma reservoir bag 28 before being recirculated through the system with a portion also being returned to the plasma separation machine 7. Reservoir bag 28 is made of a strong and pliable material, such as PVC plastic. Reservoir bag 28 includes an inlet 30 and a pair of outlets 32, 34 at the lower end of the bag. Outlet 32 provides fluid back to container 100 for further treatment, while outlet 34 leads to plasma separation machine 7. A dividing partition 36 between inlet 30 and outlets 32, 34 define a pair of compartments 38, 40. Compartment 38 provides an inlet channel and compartment 40 provides an overflow reservoir for holding a volume (e.g., 100 ml) of fluid. Dividing partition 36 between compartments 38, 40 ensures that particulate matter which may be in the plasma is trapped in compartment 38 and prevented from returning to liver assist system 5 where it may cause clogging of conduit 6 or other components of the system. Due to the increased cross-sectional area of compartment 38 (with respect to the cross-sectional area of inlet 30), the velocity of the plasma entering reservoir bag 28 decreases. Thus, the particulate matter is allowed to settle in the lower portion of compartment 38. The plasma overflowing into compartment 40 is temporarily held before being recirculated to liver assist system 5 or plasma separation machine 7. Reservoir bag 28 also serves to accommodate surging of the plasma.

Reservoir bag 28 may include multiple compartments between inlet 30 and outlets 32, 34 so that the particulate matter will settle in the bottom portions of each compartment as the plasma overflows from one compartment to the next.

A vent 48 is provided at the top of reservoir bag 28 by a tube which extends to a filter (not shown). Vent 48 allows gas within the plasma, in the form of bubbles, to escape.

The level of plasma in reservoir bag 28 can be visually observed by the operator of the system who can manually release or restrict flow of the plasma from the bag to maintain a proper level of plasma in the bag, for example, using line 15. The level can also be maintained using an electronic device which controls pump 14 of the liver assist system and/or a pump of plasma separation machine 7.

An optional filter 9 with a bypass 12 may be included within tubing 70 for filtering particulate matter from plasma returning to the external system. Filter 9 serves to capture and prevent the circulation of cells released into conduit 6 in the event of a catastrophic failure of hollow fibers 104 in container 100. Bypass 12 provides a flow path for the plasma if filter 9 becomes clogged or needs replacement.

Liver assist system 5 can also be used in a closed, off-line system operation, with reservoir bag 28 serving as the source of plasma being introduced to system 5. In this case, reservoir bag 28 will generally be larger in size, for example, 2 liters.

Referring to the lower right inset of FIG. 3, a cell inoculation device 200 includes a flexible seeding bag 202 formed of plastic (e.g. PVC) in which harvested cells to be inoculated in container 100 are held. If the cells are a replenishment of astrocytes (also called neuroglial or glial cells), they can be harvested using methods well known in the art. See, e.g., Booher et al., Neurobiology 2:97–105, 1972. Cell inoculation device 200 includes an inlet 212 through which cell suspension is dispensed within seeding bag 202 and an outlet 206 which can be connected, for example, to an inlet tube 60 of liver assist system 5. Outlet 206 is connected to a tube 208 which extends to the bottom portion of seeding bag 202 to maximize the removal of cell suspension. Seeding bag 202 is easily attached and detached from liver assist system 5 and is also a convenient receptacle for transporting the cells.

The cells are removed from seeding bag 202 into container 100 using a pressure mechanism device (not shown) attached to cell inoculation device 200. In one embodiment, the pressure mechanism device may be a pressure cuff which is wrapped around seeding bag 202. Upon manual or automatic actuation, positive pressure is provided within bag 202 causing the cells to rise through tube 208 and out of outlet 206. In another embodiment, a pressurized gas source may be used to provide positive pressure via inlet hose 204 to the inside of bag 202 causing the cells to rise through tube 208. In still a further embodiment, the cells can be extracted from bag 202 by attaching a pump to outlet 206 of tube 208 to pump the cells out of bag 202.

A rinsing tube 214 is provided at the top of bag 202 for introducing a rinsing solution (e.g., saline) to ensure the removal of residual cells that may settle within the bottom of bag.

Liver assist system 5 further includes bypass conduits which allow flexibility of use and ensure safety in case of emergency. Connection between liver assist system 5 and the plasma separation machine 7 (or other external system) includes tubing 70 which provides a path of flow for a portion of the treated plasma back to plasma separation machine 7 from outlet 34 of reservoir bag 28. A bridge section 72 connects tubing 70 to tubing 74 which introduces the plasma to be treated to container 100. When plasma separation machine 7 is used on-line with liver assist system 5, a pinch valve 76 is closed to prevent flow of plasma through bridge section 72 so that all of the plasma returning along tubing 70 flows to plasma separation machine 7. In the event of an emergency, when it becomes necessary to prevent interflow between the system 5 and machine 7, pinch valves 78, 80 are closed and pinch valve 76 is opened. In this arrangement, plasma from the plasma separation machine 7 can be directed to flow through line 11, through open pinch valve 76, and back to plasma separation machine 7 through line 13. Line 15 may be open to a plasma storage bag 47 within machine 7. Bag 47 may act as a compliant chamber to account for variations of the flow rate in and out of plasma separation machine 7 through bypass 72. Pressure transducers 82, 84 are provided within conduit 6 to sense extreme or inadequate levels of pressure. In these situations, signals from transducers 82, 84 are used to control pinch valves 76, 78, 80 and pump 14, and can also be used to provide a visual or audible warning signal to alert the operator of a dangerous condition. Sampling ports may also be provided along conduit 6 to examine the characteristics of the plasma.

Liver assist system 5 provides the following features for rinsing and priming conduit 6 and its components (i.e., oxygenator, filters, and container). Tubing 92, 93, operating in conjunction with pinch valves 94, 95, allows the introduction of two separate solutions for priming and rinsing conduit 6 and the components disposed therein. One solution (e.g., saline) is introduced through tubing 92 with the other solution (e.g., 5% dextrose) introduced through tubing 93. Bypass segments allow for flushing the components independently or in series. The components may be rinsed and primed in any order.

Tubing 92, 93 for introducing priming solution and tubing 21, 29 leading to integral waste bags 23, 31, 33, create a closed system and provide an aseptic method of rinsing and priming liver assist system 5. In one configuration, tubing 29, 92, 93 may be sealed and removed to condense liver assist system 5 once it is ready to receive plasma. The use of pinch valves 27 and 98 allows the priming solution to be directed to waste bags 31, 33 after one pass before flowing to the waste bags or recirculated through liver assist system 5. Container 100 is rinsed and primed along the fibers with the waste solution directed to waste bags 31, 33. A separate waste bag 23 is connected to container 100 at port 114. Enclosure 108 is primed, and pores of hollow fibers 104 are rinsed (FIG. 2C), with the waste solution directed to waste bag 23. When cleansing of container 100 is complete, container 100 is completely filled with saline and ready to receive astrocytes and optionally other cells.

Tubing 70, 74 between liver assist system 5 and plasma separation machine 7 is rinsed by opening valves 78, 80 for a period of time to allow some of the saline to flow through the tubing. Generally, it is important that liver assist system 5 be fully primed with the priming solution at the initiation of plasma processing.

Astrocytes, and other cells if any, from cell inoculation device 200 are then introduced at inlet line 60 and the saline within enclosure 108 of container 100 is displaced into waste bags 31, 33. Waste bags 23, 31, 33 and lines 21, 60 are then removed. In this condition, liver assist system 5 is considered to be primed and ready to receive plasma. Further details of liver assist system 5 suitable for use with container 100 containing astrocytes are found in U.S. Pat. No. 5,643,794.

Three-Compartment Container Having Astrocytes

Figure 4A:
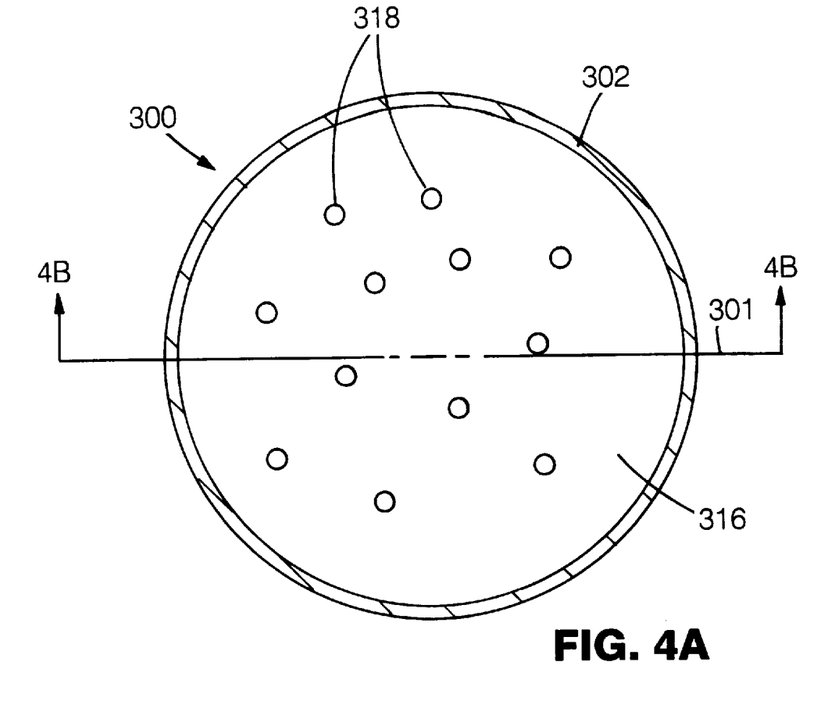
FIG. 4A is a diagrammatic top view of a container of the invention.
Figure 4B:
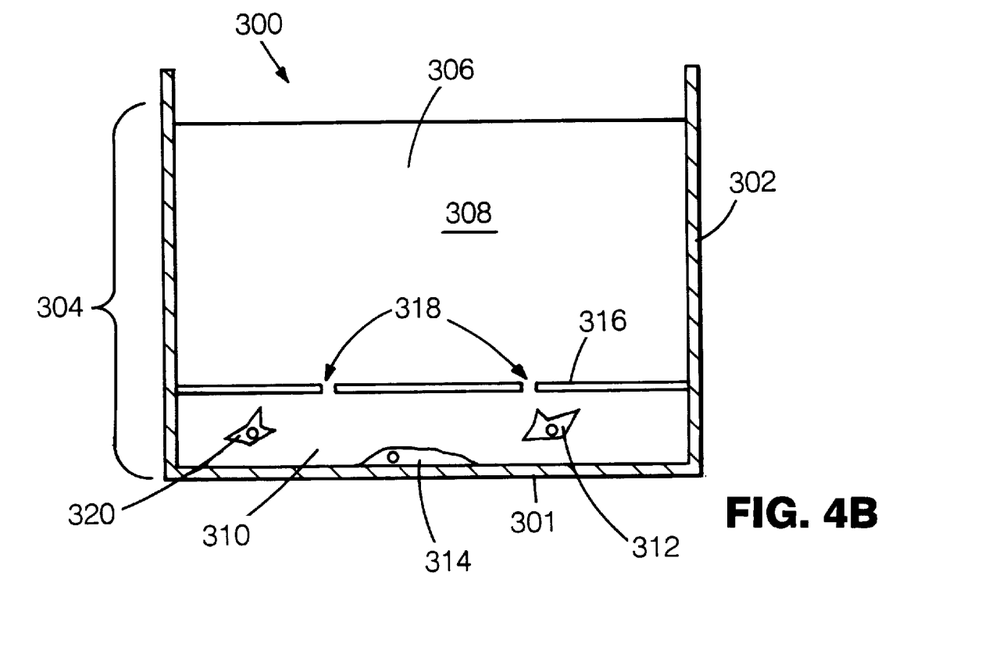
FIG. 4B is a diagrammatic cross-sectional side view of the container cut along lines 4B—4B of FIG. 4A.

A second embodiment of a container for removing toxins from a biological fluid is shown in FIGS. 4A and 4B. A container 300 for receiving a biological fluid 306 includes a base 301 and a side wall 302 which together define an internal volume 304 of the container. Container 300 as shown in FIG. 2A does not contain a biological fluid, while FIG. 2B shows container 300 partially filled with biological fluid 306. Internal volume 304 is divided, by a first porous barrier 316 and a second porous barrier 317 into a first compartment 308, a second compartment 310, and a third compartment 311. Astrocytes 312, 314 and hepatocyte 320 are deposited in third compartment 311 with astrocyte 312 and hepatocyte 320 being suspended in biological fluid 306, while astrocyte 314 is adhered to base 301. Fibroblast 321 is deposited in second compartment 310 to produce growth factors which enhance the function and viability of astrocytes 312, 314. Porous barrier 316 contains pores 318 which are small enough to block astrocytes 312, 314, hepatocyte 320, and fibroblast 321 from passing from second compartment 310 or third compartment 311 through porous barrier 316 into first compartment 308. Porous barrier 317 contains pore 319 which is small enough to block fibroblast 321 from passing from second compartment 310 through porous barrier 317 into third compartment 311.

In operation, biological fluid 306 is poured into internal volume 304 to contact astrocytes 312, 314, hepatocyte 320, and fibroblast 321. Once contact between biological fluid 306 and astrocytes 312, 314 and hepatocyte 320 is sufficient to remove toxins from biological fluid 306, the processed biological fluid 306 is poured from container 300 into an intravenous bag (not shown) for administration into a patient (not shown). The removal of toxins from biological fluid 306 can be monitored by any method well known in the art, depending on the nature of the toxin and the eventual use of the biological fluid.

Clearance of Ammonia by Astrocytes

Four identical devices including a bioreactor seeded with astrocytes were assembled. Each device consisted of silicone tubing, a pump, approximately 200 ml of Dulbecco's Modified Eagle Medium supplemented with 10% fetal calf serum and antibiotics, and a hollow fiber container seeded with astrocytes (similar to container 100 described above). The astrocytes were obtained from 16 one-day old rat pups following the procedure described in Booher et al., supra. Astrocytes from four pups were placed into the shell side of each bioreactor and allowed to grow while medium was provided to the lumenal side of the bioreactor at a flow rate of 10 ml/min. The device was maintained at 37° C.

Samples of medium were periodically withdrawn and analyzed for ammonium. After 30 minutes of observation to establish a base line, 5 mM ammonia was added into the circulating medium, resulting in a peak concentration of about 6.7 mg/dL ammonia in the medium. During the subsequent 20 minutes, ammonia was reduced in the circulating medium, establishing the ability of astrocytes to remove a toxin from a biological fluid. The reduction of ammonia was unexpected, since living cells in culture tend to produce ammonia, thereby raising the ammonia level in the medium, rather than reduce the ammonia level.

To assay astrocyte viability, the withdrawn medium was also analyzed for lactate dehydrogenase (LDH) activity, a surrogate marker for cell death. LDH activity was measured in serum-free culture medium at room temperature using the method generally described in Worblewski et al., Proc Soc Exp Biol Med 90:210–213, 1955. This method was modified as follows. Growth media was collected from culture plates, and cells were harvested in 0.5% Triton X-100. Following centrifugation at 2000× g for 5 minutes, the supernatants of both cell and media components were assayed for LDH by spectrophotometry. The level of LDH activity did not significantly decrease during the time of observation for this experiment, indicating that the astrocytes were viable.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. For example, liver assist system 5 can be used in other medical applications, such as to remove toxins from a batch of synthetic blood. In addition, the compartments of container 100 (i.e., lumenal spaces 112 and enclosure 108) and container 300 (i.e., first compartment 308 and second compartment 310) of the invention can be in any orientation such that at least one region of one compartment is adjacent to a region of another compartment. Therefore, the container includes an arrangement in which the second compartment is enclosed by the first compartment, the porous barrier being a bag holding the astrocytes. Thus, other embodiments are also within the claims.

What is claimed is:

1. A system for treating a biological fluid comprising:

a first container having a first port for receiving the biological fluid and a second port through which the biological fluid exits the first container, a conduit connected to the first port and the second port, and astrocytes residing in the first container.

2. The system of claim 1, said conduit comprising a first plurality of hollow fibers disposed within the first container, each of the hollow fibers defining a first lumenal space through which the biological fluid passes, and wherein the astrocytes reside outside of the first lumenal space.

3. The system of claim 2, wherein the hollow fibers are formed of a membrane material having pores with a diameter of less than about 2 $\mu$m.

4. The system of claim 3, wherein the pores are about 0.1 $\mu$m to 1 $\mu$m in diameter.

5. The system of claim 3, wherein the plurality of hollow fibers are arranged parallel to each other and along a longitudinal axis of the container.

6. The system of claim 1, further comprising a second container connected within the conduit, the second container having a third port for receiving the biological fluid and a fourth port through which the biological fluid exits the second container; and non-astrocyte cells residing in the second container.

7. The system of claim 6, wherein the non-astrocyte cells are hepatocytes.

8. The system of claim 6, further comprising a second plurality of hollow fibers disposed within the second container, each of the hollow fibers of the second plurality defining a second lumenal space through which the biological fluid passes, and wherein the non-astrocyte cells reside outside of the second lumenal space.

9. The system of claim 1, wherein the biological fluid includes plasma.

10. The system of claim 1, further comprising non-astrocyte cells residing in the first container.

11. The system of claim 10, wherein the non-astrocyte cells are hepatocytes.

12. The system of claim 1, wherein the astrocytes are rat astrocytes.

13. A container for treating a biological fluid comprising:

a first compartment for receiving the biological fluid, a second compartment adjacent to the first compartment, a first porous barrier which separates the first compartment from the second compartment, the first porous barrier being impermeable to the astrocytes, and astrocytes residing in the second compartment.

14. The container of claim 13, further comprising:

a third compartment adjacent to the first compartment or second compartment, a second porous barrier which separates the third compartment from the first compartment or second compartment, the second porous barrier being impermeable to non-astrocyte cells, and non-astrocyte cells residing in the third compartment.

15. The container of claim 13, further comprising non-astrocyte cells residing in the second compartment, the first porous barrier being impermeable to the non-astrocyte cells.

16. The container of claim 13, wherein the biological fluid includes plasma.

17. The system of claim 1, wherein the biological fluid is whole blood.

18. The container of claim 13, wherein the biological fluid is whole blood.

* * * * *